United States Patent
Borgen et al.

(10) Patent No.: US 10,481,080 B2
(45) Date of Patent: Nov. 19, 2019

(54) OPTICAL ELEMENTS IN GAS SENSORS

(71) Applicant: GASSECURE AS, Oslo (NO)

(72) Inventors: Lars Borgen, Sande i Vestfold (NO); Britta Fismen, Oslo (NO); Thor Christian Hobæk, Oslo (NO); Håkon Sagberg, Oslo (NO)

(73) Assignee: GASSECURE AS, Oslo (NO)

( * ) Notice: Subject to any disclaimer, the term of this patent is extended or adjusted under 35 U.S.C. 154(b) by 8 days.

(21) Appl. No.: 15/737,243

(22) PCT Filed: Jun. 16, 2016

(86) PCT No.: PCT/GB2016/051786
§ 371 (c)(1),
(2) Date: Dec. 15, 2017

(87) PCT Pub. No.: WO2016/203233
PCT Pub. Date: Dec. 22, 2016

(65) Prior Publication Data
US 2018/0202920 A1    Jul. 19, 2018

(30) Foreign Application Priority Data
Jun. 16, 2015    (GB) .................................. 1510563.8

(51) Int. Cl.
*G01N 21/15*    (2006.01)
*G01N 21/3504*    (2014.01)

(52) U.S. Cl.
CPC ......... *G01N 21/15* (2013.01); *G01N 21/3504* (2013.01); *G01N 2021/158* (2013.01)

(58) Field of Classification Search
CPC ............... G01N 21/15; G01N 21/3504; G01N 2021/158

USPC ................................ 356/437, 440, 326, 301
See application file for complete search history.

(56) References Cited

U.S. PATENT DOCUMENTS

| | | | |
|---|---|---|---|
| 3,998,592 | A | 12/1976 | Pyle |
| 4,213,703 | A | 7/1980 | Haunold et al. |
| 4,440,497 | A | 4/1984 | Carey et al. |
| 8,120,777 | B2 | 2/2012 | Weinberger et al. |

(Continued)

FOREIGN PATENT DOCUMENTS

| | | |
|---|---|---|
| EP | 1998164 A1 | 12/2008 |
| JP | 2006058009 A | 3/2006 |

OTHER PUBLICATIONS

International Search Report and Written Opinion dated Sep. 1, 2016 in corresponding International Application No. PCT/GB2016/051786, 21 pages.

(Continued)

*Primary Examiner* — Isiaka O Akanbi
(74) *Attorney, Agent, or Firm* — Haley Guiliano LLP (57) ABSTRACT

A gas sensing apparatus (48) comprises a gas sensor arranged to use light to sense presence of a gas; an optical element (12, 40) arranged so that said light impinges thereon; and a thermoelectric heat pump (2, 24) having a cold side (6, 36) and a hot side (8, 34). The thermoelectric heat pump (2, 24) is configured to transfer heat energy from said cold side (6, 36) to said hot side (8, 34) in response to a supply of electrical energy provided to the thermoelectric heat pump (2, 24). The hot side (8, 34) of the thermoelectric heat pump (2, 24) is in thermal contact with the optical element (12, 40).

21 Claims, 6 Drawing Sheets

(56) References Cited

U.S. PATENT DOCUMENTS

| | | | |
|---|---|---|---|
| 2006/0033980 A1* | 2/2006 | Wagner | G02B 7/008 |
| | | | 359/291 |
| 2007/0227710 A1* | 10/2007 | Belady | H05K 7/2079 |
| | | | 165/122 |
| 2009/0095918 A1* | 4/2009 | Iwase | G01N 21/031 |
| | | | 250/432 R |
| 2009/0112482 A1* | 4/2009 | Sandstrom | G01N 21/6452 |
| | | | 702/19 |
| 2010/0238446 A1* | 9/2010 | Akiyama | G01N 21/031 |
| | | | 356/437 |
| 2012/0199745 A1 | 8/2012 | Flanders et al. | |
| 2012/0287418 A1 | 11/2012 | Scherer et al. | |

OTHER PUBLICATIONS

UK Intellectual Property Office Search Report dated Oct. 28, 2015 in corresponding GB Patent Application No. 1510563.8, 3 pages.
Tellurex, "Frequently Asked Questions About Our Cooling and Heating Technology," pp. 1-20, 2010, www.Tellurex.com.

* cited by examiner

OPTICAL ELEMENTS IN GAS SENSORS

CROSS REFERENCE TO RELATED APPLICATION

This application is a national stage entry of International Application No. PCT/GB2016/051786, filed on Jun. 16, 2016, which claims the benefit of and priority to GB Patent Application No. 1510563.8, filed on Jun. 16, 2015, the entire contents of each of which are hereby incorporated by reference herein in their entireties.

This invention relates to prevention and/or removal of condensation on optical elements in gas sensors, and in particular, the use of thermoelectric heat pumps to prevent or remove condensation.

Gas sensors are used in a variety of applications where it is necessary or desirable to detect the presence of a particular gas or gases. For example, in industries using explosive gases, it is necessary to monitor surrounding areas to ensure that there are no gas leaks that could result in an explosion due to ignition of the gas.

A type of gas sensor known in the art determines the presence of a gas by detecting changes in the spectrum of electromagnetic radiation due absorption by the gas. Such a gas sensor typically comprises a gas measurement volume contained within a gas sensor housing. The housing has apertures to allow gas to pass in and out of the gas measurement volume. Electromagnetic radiation is passed through the gas measurement volume from a radiation source to a radiation detector. The electromagnetic radiation has a frequency band spectrum that covers frequencies corresponding to an absorption band of the gas of interest. The frequency spectrum received at the detector is analysed to determine whether any radiation has been absorbed within the absorption band frequency range. If radiation has been absorbed in the absorption band frequency range, this indicates that the gas of interest may be present in the gas measurement volume. The analysis of the frequency spectrum of the electromagnetic radiation may involve comparing the absorption at frequencies in an absorption band with the absorption at frequencies within a reference band, where the reference band is a portion of the frequency spectrum of the electromagnetic radiation that is not absorbed by the gas of interest.

In such gas sensors, it is common for the electromagnetic radiation to be passed through or reflected from optical elements such as windows and mirrors. However, as it is necessary to allow ambient atmosphere to enter the measurement volume in order to sense gas in the ambient atmosphere, it is not possible to prevent water vapour from entering the measurement volume. In certain environmental conditions, condensation can form on the optical elements. Condensation forms when the temperature of ambient air adjacent a surface is at a higher temperature than the surface. Condensation is therefore likely to form when the ambient temperature varies. For example, if the gas sensor cools down (e.g. overnight), the housing and optical elements will thermalize with the surroundings and become cold. When the temperature rises (e.g. during the day) the ambient temperature will increase, but it will take some time for the housing and optical surfaces to thermalize, resulting in the housing and optical surfaces being colder than the ambient temperature. Condensation will then form on the relatively cold surfaces of the optical element. The problem may be exacerbated when there is high humidity.

Condensation on optical elements is problematic in gas sensors because when the electromagnetic radiation passes through the windows or is reflected from the mirrors, the condensation affects the spectrum of light that is transmitted or reflected. The gas detection method relies on measuring a change in the electromagnetic spectrum due to absorption by the gas. If there is also an unpredictable amount of absorption or scattering due to condensation on the optical elements, it is difficult or impossible to reliably determine whether or not a gas is present. Condensation on optical elements may cause false positive readings, or may result in the gas sensor failing to detect the presence of a gas. The former case is at least inconvenient, as it may lead a person monitoring the system to believe that there is a dangerous gas condition present when there is not, and the latter situation can be potentially dangerous if a dangerous gas leak goes undetected because the gas sensor has condensation on its optical elements.

A solution that has been applied in the art to ameliorate this problem is to provide a respective resistive heating element in thermal contact with each optical element.

As mentioned above, when the temperature of an optical element is lower than the ambient air temperature, especially if the humidity is high, water vapour will condense on the surfaces of the optical elements. When this occurs, the condensation can be prevented or removed by switching on the resistive heating elements in contact with the optical elements. The heating elements transfer thermal energy to the optical elements, thereby raising their temperature. Once their temperature is higher than the ambient temperature, condensation on the optical elements evaporates. Condensation can similarly be prevented from forming on an optical element by using a resistive heating element to heat the optical element before condensation forms.

However, this approach has problems associated with it. Due to the nature of the locations requiring gas monitoring, it is not always possible to conveniently locate gas sensors at locations with access to a power supply. Accordingly, it is common to need to rely on battery power to operate gas sensors. However, the amount of battery power required to run resistive heating elements is relatively high. This results in a significant reduction of the battery life of the gas sensor.

This is particularly problematic in gas sensor networks comprising a large number of gas sensor units, which may be spread over a large area and could result in a product not being commercially acceptable.

It is therefore an object of the present invention to provide a more efficient apparatus for preventing condensation on optical elements of gas sensors.

When viewed from a first aspect the invention provides a gas sensing apparatus comprising:
  a gas sensor arranged to use light to sense presence of a gas;
  an optical element arranged so that said light impinges thereon; and
  a thermoelectric heat pump having a cold side and a hot side, wherein the thermoelectric heat pump is configured to transfer heat energy from said cold side to said hot side in response to a supply of electrical energy provided to the thermoelectric heat pump, and wherein the hot side of the thermoelectric heat pump is in thermal contact with the optical element.

The invention extends to a method of preventing, removing or reducing condensation on an optical element in a gas sensing apparatus, wherein the gas sensing apparatus comprises a gas sensor arranged to use light to sense presence of a gas and wherein the optical element is arranged so that said light impinges thereon, the method comprising:

using a thermoelectric heat pump to transfer heat energy to the optical element, wherein:

the thermoelectric heat pump has a cold side and a hot side, and the thermoelectric heat pump transfers heat energy from said cold side to said hot side in response to a supply of electrical energy provided to the thermoelectric heat pump; and the hot side of the thermoelectric heat pump is in thermal contact with the optical element.

It will be appreciated that the terminology "hot side" and "cold side" is used herein in accordance with the commonly understood meanings in the art, which is that the "cold" side absorbs heat energy, and the "hot" side emits heat energy, so that heat energy is pumped from the cold side to the hot side. It is not necessarily the case that the hot side is at a higher temperature than the cold side. Depending on operating and ambient conditions (e.g. humidity level), the hot side may be at a lower temperature than the cold side.

In addition, the use of the term "side" in the context of the hot side and the cold side means a surface or part of the thermoelectric heat pump, and does not limit the thermoelectric heat pump to any particular shape. A thermoelectric heat pump refers to any solid state device that uses the thermoelectric effect to transfer heat from one part of the device to another upon the application of an electric current.

The term "thermoelectric heat pump" therefore encompasses thermoelectric heaters and thermoelectric coolers (which may also be referred to as Peltier heaters, Peltier coolers, or Peltier heat pumps).

It will also be appreciated that the term "light" is used herein to mean electromagnetic radiation, i.e. the light may be, but is not necessarily, visible light. The light may have any suitable frequency or range(s) of frequencies.

The Applicant has appreciated that in order to avoid condensation on optical elements in a gas sensing apparatus, even with 100% relative humidity, the optical element surfaces only need to be slightly warmer than the ambient air to avoid condensation. For example, a difference of 0.2° C. may be sufficient to avoid condensation, although it will be appreciated that the invention is not limited to a temperature difference of 0.2° C. Due to the very small temperature difference required, thermoelectric heat pumping is very efficient. In addition to the active heat pumping by the thermoelectric heat pump, there is also additional heat energy resulting from Joule heating due to the electrical resistance of the thermoelectric heat pump itself. This additional heat energy contributes to the increase in temperature of the optical element.

In preferred embodiments, the gas sensing apparatus comprises a heat sink in thermal contact with the cold side of the thermoelectric heat pump. The method preferably comprises using the thermoelectric heat pump to transfer heat energy from the heat sink to the optical element. Any suitable heat sink may be used. In preferred embodiments, the heat sink extends along substantially all of a length, and/or substantially all of a width, and/or substantially all of a depth of a measurement volume of the gas sensing apparatus. The heat sink may be any type known in the art, for example, the heat sink may have fins and/or a corrugated shape. It may be made of metal or any other suitable material or combination of materials. The heat sink may be made from a porous ceramic material. The Applicant has appreciated that this is particularly advantageous, as a heat sink made from porous ceramic material can be very effective at transferring heat, e.g. more effective than metal, due to the large surface area of the porous material.

It will be appreciated that the term "heat sink" refers to a structure that may be suitable for conventional use as a heat sink, that is with a shape intended to maximise surface area and airflow over it, but that the heat flow in the heat sink in accordance with the present invention is in the opposite direction compared with conventional use of a heat sink. In a conventional heat sink arrangement, the heat sink is used to draw heat away from hot body (e.g. a component) to cool the body down. The heat is conducted away through the heat sink and is transferred from its surface to the ambient air. However, in accordance with the present invention, the heat sink draws heat from the ambient air, and the heat is conducted through the heat sink to a cold body (i.e. an optical element) to warm up the body. The underlying considerations are, however, the same.

The heat sink provides a further advantage, which contributes to the efficiency of the gas sensing apparatus. In embodiments comprising a heat sink, in addition to raising the temperature of the optical element, the thermoelectric heat pump takes heat energy from the heat sink, which in turns takes heat energy from the ambient air, lowering the ambient air temperature in the immediate locality. As condensation forms when the air adjacent a surface is warmer than the surface, lowering the air temperature also serves to prevent or remove condensation. The thermoelectric heat pump therefore provides two complementary effects that help to bring the optical element to a higher temperature than the ambient air: it raises the temperature of the optical element and it lowers the temperature of the ambient air.

A further effect of the heat sink that contributes to the removal and/or prevention of condensation is that the heat sink serves as a condensation trap. When heat energy is pumped away from the heat sink, it becomes cold relative to the ambient air. Water vapour in the ambient air therefore condenses on the heat sink, reducing the humidity of the local ambient air, helping to prevent and/or remove condensation on the optical element. In addition, when water vapour condenses on the heat sink, heat energy is transferred to the heat sink. This energy release due to the condensation on the heat sink is then pumped to the optical element by the thermoelectric heat pump, and therefore contributes to the heating of the optical element. The heat sink may have a surface coating or a surface micro- or nano-structure. For example, the heat sink may be porous. This may enhance water adsorption and improve the heat sink's efficacy as a condensation trap, helping to reduce the humidity of the ambient air. It may also increase the energy release due to condensation on the heat sink.

It will be appreciated that in embodiments without a heat sink, the above-mentioned benefits are provided to an extent by the cold side of the thermoelectric heat pump. In those embodiments, the cold side draws heat energy directly from the local ambient air, cooling the air. The cold side may also serve as a condensation trap, and energy from water vapour condensing on the cold side may contribute to the heating of the optical element in the way described above. However, these effects may be enhanced by providing a heat sink due to the large surface area of a heat sink.

A gas sensing apparatus according to the present invention comprises at least one optical element. However, in a set of embodiments, the gas sensing apparatus comprises more than one optical element in total. Each optical element may be selected from the group consisting of a mirror and a window, although other optical elements may be used.

One or more additional thermoelectric heat pumps may be provided. Preferably, each of the additional heat pumps is arranged to have its respective hot side in thermal contact with one of the one or more additional optical elements. In some embodiments, the cold side of each of the additional thermoelectric heat pumps is in thermal contact with the heat sink.

In some embodiments, irrespective of the number of optical elements or the number of thermoelectric heat pumps, one or more additional heat sinks may be provided. Accordingly, the thermoelectric heat pump may also have its cold side in thermal contact with one, some or all of the additional heat sinks. Where the gas sensing apparatus comprises additional thermoelectric heat pump(s), the additional thermoelectric heat pump(s) may have their cold sides in thermal contact with one or more of the additional heat sinks.

Preferably the hot side of the thermoelectric heat pump is in thermal contact with the optical element by virtue of being in physical contact. The hot side of the thermoelectric heat pump may be in direct physical contact with the optical element, or may be in contact via an intermediate thermally conducting element or substance, for example via a thermally conductive bonding material or adhesive. Preferably, however, the hot side of the thermoelectric heat pump is held in direct physical contact with the optical element. For example, the thermoelectric heat pump and the optical element may be held together using a mechanical fixing arrangement, such as screws or clamps.

Similarly, the cold side of the thermoelectric heat pump is preferably in thermal contact with the heat sink by virtue of being in physical contact therewith. The cold side of the thermoelectric heat pump may be in direct physical contact with the heat sink, or may be in contact via an intermediate thermally conducting element or substance, for example via a thermally conductive bonding material or adhesive. The cold side of the thermoelectric heat pump may be in thermal contact with the heat sink via a thermal conductor (e.g. an extended thermal conductor or "heat pipe"). This may allow greater freedom of design in terms of the position of the heat sink. Preferably, however, the cold side of the thermoelectric heat pump is held in direct physical contact with the heat sink. For example, the thermoelectric heat pump and the heat sink may be held together using a mechanical fixing arrangement, such as screws or clamps.

The thermoelectric heat pump may have any suitable shape. It may be formed from a square or rectangular array of alternating n- and p-type pellets on a ceramic substrate, with a further ceramic substrate overlaid on the pellets, so that the thermoelectric heat pump has a square or rectangular shape. However, other shapes are possible. The thermoelectric heat pump may have an aperture or gap for allowing electromagnetic radiation to pass through. For example, the thermoelectric heat pump may be a ring shape, or a C shape. This is particularly advantageous when the thermoelectric heat pump is used with a window, as it allows electromagnetic radiation to pass through the window via the aperture or gap, while allowing the hot side of the thermoelectric heat pump to be in thermal contact with (and thereby to heat) the area of the window surrounding, or substantially surrounding, the area through which the radiation passes. Similarly, a thermoelectric heat pump having an aperture or gap can be advantageously used with a mirror, as it allows the thermoelectric heat pump to be fixed to the reflective side of the mirror, rather than to the rear of the mirror, without blocking the passage of radiation (as the radiation can pass through the gap or aperture). This may provide more efficient heating of the reflective side of the mirror.

In a set of embodiments the gas sensing apparatus comprises a measurement volume. The gas sensing apparatus may comprise a housing, and holes may be provided in the housing to allow ingress of gas into the measurement volume. Preferably the thermoelectric heat pump and, where provided, the heat sink are disposed in the measurement volume. For example, they may be arranged to heat a mirror in the measurement volume, or a window between the measurement volume and another volume of the gas sensing apparatus. However, it is not essential for the gas sensing apparatus to comprise a measurement volume. For example, the gas sensing apparatus may be an open-path detector. The thermoelectric heat pump and/or heat sink therefore may not necessarily be disposed in a measurement volume. Further, even in embodiments with a measurement volume, the thermoelectric heat pump may be used to heat an optical element (or a surface of an optical element) that is not inside the measurement volume. Accordingly, even in embodiments with a measurement volume, the heat sink may be disposed in a volume of the gas sensing apparatus other than the measurement volume.

Preferably the optical element is thermally insulated from the housing. It may be mounted on a thermally insulating structure. For example, a mirror may be fixed to a thermally insulating mount, where the thermally insulating mount is fixed to a wall of the housing. The mirror may be held in place by a mirror holder, e.g. which may clamp or pin the mirror in place. The mirror holder may be made of a thermally insulating material, e.g. plastic. Additionally or alternatively, the mirror holder may have a small area of contact with the mirror. For example, the mirror holder may comprise a small number (e.g. six or fewer) of supporting or pinning elements, e.g. pins, tabs or pegs, that hold the mirror at a number of discrete points. For example, the mirror may be mounted on or held in position in the housing using a number of pins, e.g. three pins.

In one possible arrangement, the mirror holder forms part of the heat sink, e.g. it may be integrally formed with the heat sink, or it may be thermally connected to the heat sink and made from the same material as the heat sink. In such arrangements, the mirror may be substantially thermally insulated from the heat sink by virtue of having a small contact area with the mirror holder as described above. In some embodiments, the heat sink, thermoelectric heat pump and mirror are arranged in a stack, with the heat sink extending around to the front of the mirror to pin it against the thermoelectric heat pump and the heat sink. The heat sink may then be mounted on the housing via a thermally insulating mount.

Other optical elements may be held in place by a holder, which may have any of the features described above with reference to the mirror holder.

A window may be mounted in a thermally insulating interior wall of the gas sensing apparatus. This thermal insulation is to prevent or substantially reduce heat transfer between the optical element and the housing, which may have a high heat capacity, and (like the optical elements) is likely to be colder than the ambient air in circumstances where condensation is likely. This is advantageous as it prevents heat energy that is transferred to the optical element to heat up the optical element from being dissipated in the housing.

Similarly, the heat sink is preferably thermally insulated from the housing to prevent or substantially reduce heat energy being transferred from the heat sink to the housing. It is undesirable for heat energy from the heat sink to be transferred to the housing, as this may lower the heat sink temperature. The efficiency of the thermoelectric heat pump depends on the temperature difference between the cold side (and therefore the heat sink) and the hot side. If the heat sink is cooled down due to heat transfer to the housing, then the heat sink may be significantly (e.g. several degrees) lower in temperature than the hot side of the thermoelectric heat pump, resulting in a low pumping efficiency. This is because when the temperature difference between the hot and cold sides of the heat pump is large, Joule heating dominates over thermoelectric heat transfer, and Joule heating is significantly less efficient than thermoelectric heat transfer.

It will be appreciated that the present invention may be used to remove, reduce and/or prevent condensation, and that if the thermoelectric heat pump is turned on in anticipation of the presence of condensation, it is possible to prevent condensation forming at all, rather than merely removing it once it has already formed. It is desirable to avoid condensation entirely, which could be achieved by having the thermoelectric heat pump operating continuously. However, it will also be appreciated that continuous operation will deplete battery power more quickly than intermittent use. Therefore, although the thermoelectric heat pump may be switched on continuously, preferably it is switched on intermittently.

The thermoelectric heat pump may be switched on at pre-determined, e.g. regular, intervals, for example, in response to a timer. It may be switched on at pre-determined times, e.g. specific times of day when condensation is more likely (e.g. in the morning). It may be switched on in response to an environmental condition, e.g. a measured change in ambient temperature or humidity. It may be switched on in response to the detection of a condition indicating the presence of condensation. The gas sensing apparatus may be configured to determine the presence of condensation from data for detecting a gas. For example, in some embodiments, the gas sensor measures values indicative of the absorption of electromagnetic radiation in one or more gas absorption bands and in one or more reference bands. Certain changes in the absorption may indicate the presence of condensation, e.g. an unexpected increase in absorption in the reference band(s), or in both the reference band(s) and the absorption band(s). The gas sensing apparatus may determine the presence (or the likelihood of the presence) of condensation from these changes in the absorption, and may then cause the thermoelectric heat pump to be switched on.

Similarly, the thermoelectric heat pump may be switched off in response to the detection (by the gas sensor or otherwise) that the condensation has been eliminated or sufficiently reduced. It may be switched off in response to a change in environmental conditions. It may be switched off once a pre-determined amount of time has elapsed.

The optional features of the thermoelectric heat pump, the optical element and the heat sink as described above may also apply respectively to the additional thermoelectric heat pump(s), the additional optical element(s), and the additional heat sink(s), where provided.

Certain preferred embodiments will now be described, by way of example only, with reference to the accompanying drawings, in which.

Figure 1:
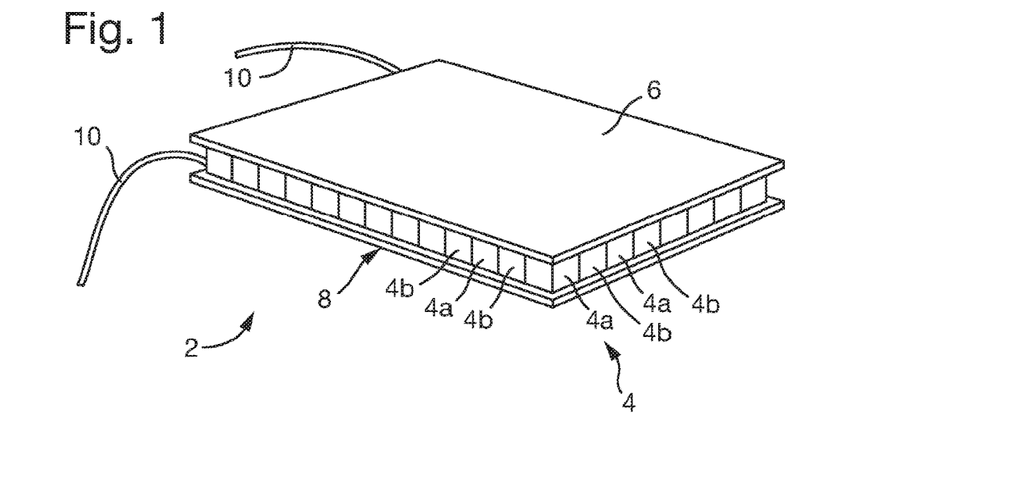
FIG. 1 shows a Peltier heater for use in a gas sensing apparatus according to embodiments of the present invention.

FIG. 1 shows a Peltier heater 2 for use in embodiments of the present invention. The Peltier heater 2 comprises a body 4 having a cold side 6 and a hot side 8. The Peltier heater is a solid state device which, in response to an electrical current supplied via electrical connections 10, transfers heat from the cold side 6 to the hot side 8. It will be appreciated that the labels "cold" and "hot" do not necessarily imply that the hot side is at a higher temperature than the cold side. In some arrangements of the present invention, particularly in humid conditions, the cold side may be warmer than the hot side. The labels cold and hot indicate the direction of heat transfer, which is from the cold side to the hot side.

The body 4 of the Peltier heater 2 may have any suitable shape. It will be appreciated that Peltier heaters are commonly rectangular or square, but other shapes are not excluded from the present invention. The Peltier heater comprises an array of alternating n-type 4a and p-type 4b thermoelectric elements arranged on a rectangular ceramic substrate (corresponding to the hot side 8). A similar rectangular ceramic substrate (corresponding to the cold side 6) is overlaid on the array.

Figure 2:
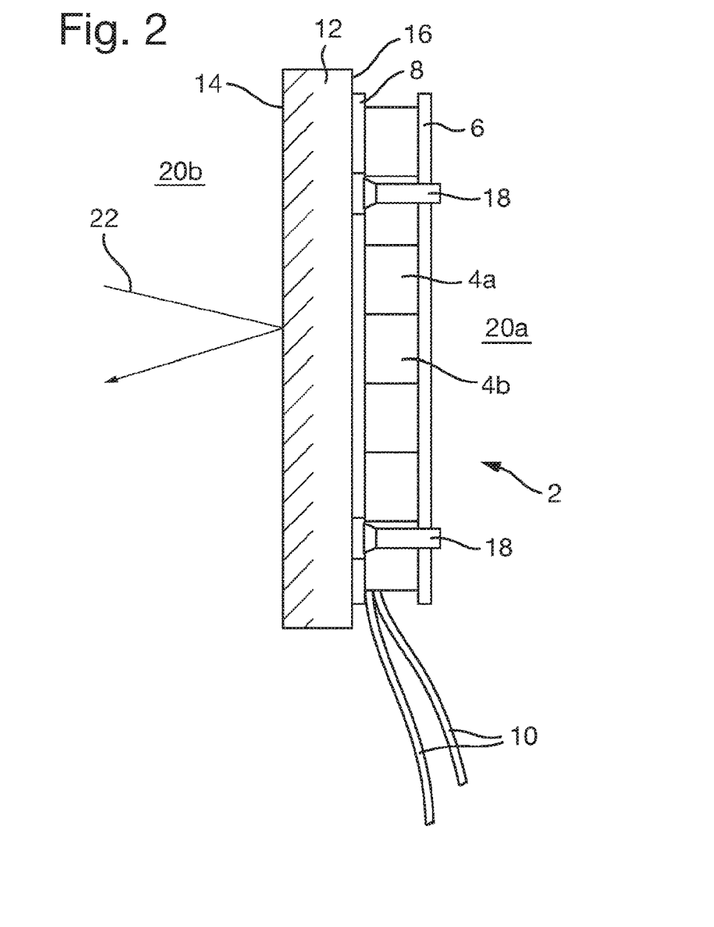
FIG. 2 shows the Peltier heater of FIG. 1 in thermal contact with the rear surface of a mirror of a gas sensing apparatus according to embodiments of the invention.

FIG. 2 shows the Peltier heater 2 of FIG. 1 arranged in thermal contact with a mirror 12. The mirror has a front (reflective) surface 14 and a rear (non-reflective) surface 16. The Peltier heater 2 is arranged so that its hot side 8 is in thermal contact with the rear surface 16 of the mirror 12. In the arrangement shown in FIG. 2, the Peltier heater 2 is held in place on the rear surface 16 of the mirror 14 by clamps 18, which are screwed in place to the rear surface 16 of the mirror 14. However, it will be appreciated that alternative methods for securing the Peltier heater 2 to the mirror 12 may be used. For example a thermally conductive adhesive could be used. When electrical current is supplied to the electrical connections 10 of the Peltier heater 2, heat energy is transferred from the cold side 6 of the Peltier heater 2 to the hot side 8.

A heat sink is provided in thermal contact with the cold side 6 of the Peltier heater 2. The heat sink is omitted from FIG. 2 for clarity, but is shown in and described below with reference to FIGS. 5 and 6. The heat transfer from the cold side 6 to the hot side 8 of the Peltier heater results in heat energy being drawn from the air surrounding the cold side, primarily via the heat sink, and being transferred to the mirror 12, thereby raising the temperature of the mirror 12. The increased temperature of the mirror 12 relative to the ambient air 20 prevents condensation forming on the front surface 14 of the mirror 12. Electromagnetic radiation 22 that is used for gas sensing can then be reflected from the front surface 14 of the mirror 12 without the spectrum of the radiation 22 being affected by condensation.

Figure 3:
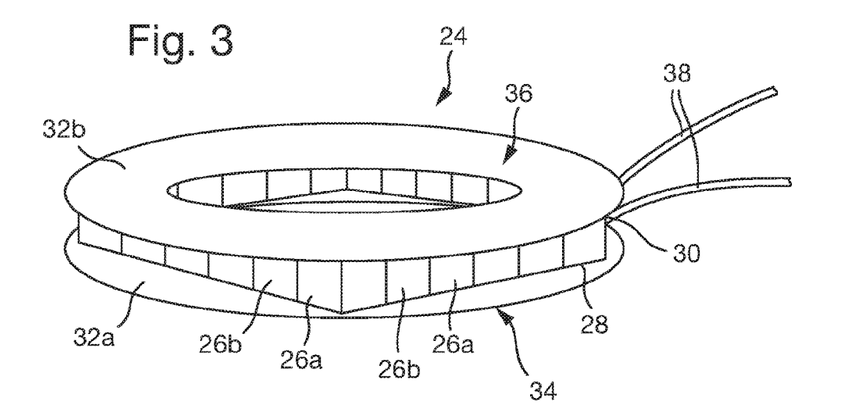
FIG. 3 shows a ring-shaped Peltier heater for use with a window or mirror in accordance with embodiments of the present invention.

FIG. 3 shows a ring-shaped Peltier heater 24 for use in embodiments of the present invention. The ring-shaped Peltier heater comprises a plurality of n-type 26a and p-type 26b thermoelectric elements arranged on a ring-shaped ceramic substrate 32a, with a further ring-shaped ceramic substrate 32b overlaid on the thermoelectric elements 26a, 26b. The ring-shaped Peltier heater 24 has a hot side 34, a cold side 36, and electrical connections 38. Similarly to the Peltier heater 2 described in FIG. 1, when an electrical current is supplied to electrical connections 38, heat is transferred from the cold side 36 to the hot side 34.

Figure 4:
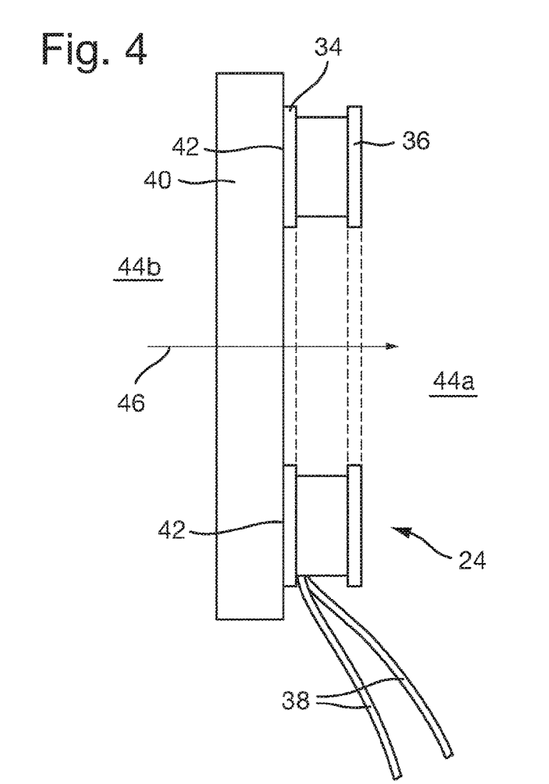
FIG. 4 shows the Peltier heater of FIG. 3 arranged in thermal contact with a window of a gas sensing apparatus according to embodiments of the present invention.

FIG. 4 shows the Peltier heater 24 of FIG. 3 arranged in thermal contact with a window 40. The Peltier heater 24 is held in contact with the window 40 by thermally conductive adhesive 42. It will be appreciated that in other embodiments alternative methods could be used for attaching the Peltier heater 24 to the window 40. In a gas sensing apparatus according to embodiments of the invention, a heat sink is provided in thermal contact with the cold side 36 of the Peltier heater 24. The heat sink is omitted from FIG. 4 for clarity but is described further below with reference to FIGS. 5 and 6.

When electrical current is supplied to the electrical connections 38, heat energy is transferred from the cold side 36 to the hot side 34 of the Peltier heater 24. Accordingly, heat is drawn from the ambient air 44a adjacent the cold side, primarily via the heat sink (not shown), and is transmitted into the body of the window 40. This raises the temperature of the window 40.

Due to the increased temperature of the window 40 compared with the ambient air 44a and the ambient air 44b on the other side of the window 40, condensation is prevented from forming on the window 40. Accordingly, when electromagnetic radiation 46 is passed through the window 40 during operation of the gas sensing apparatus, the radiation 46 is able to pass through the window 40 without alteration to its spectrum by condensation on the window 40. The reliability of the gas sensing apparatus thereby is significantly improved.

In accordance with both arrangements shown in FIGS. 2 and 4, in addition to the transfer of heat by the Peltier heater 2, 24, there is also Joule heating in the Peltier heater 2, 24. Energy generated by Joule heating is transferred to the mirror 12 or window 40 in addition to heat transferred by the Peltier effect. This provides additional heating of the mirror 12 and window 40. This additional heating contributes to the high efficiency of the Peltier heater arrangement for preventing condensation.

Figure 5:
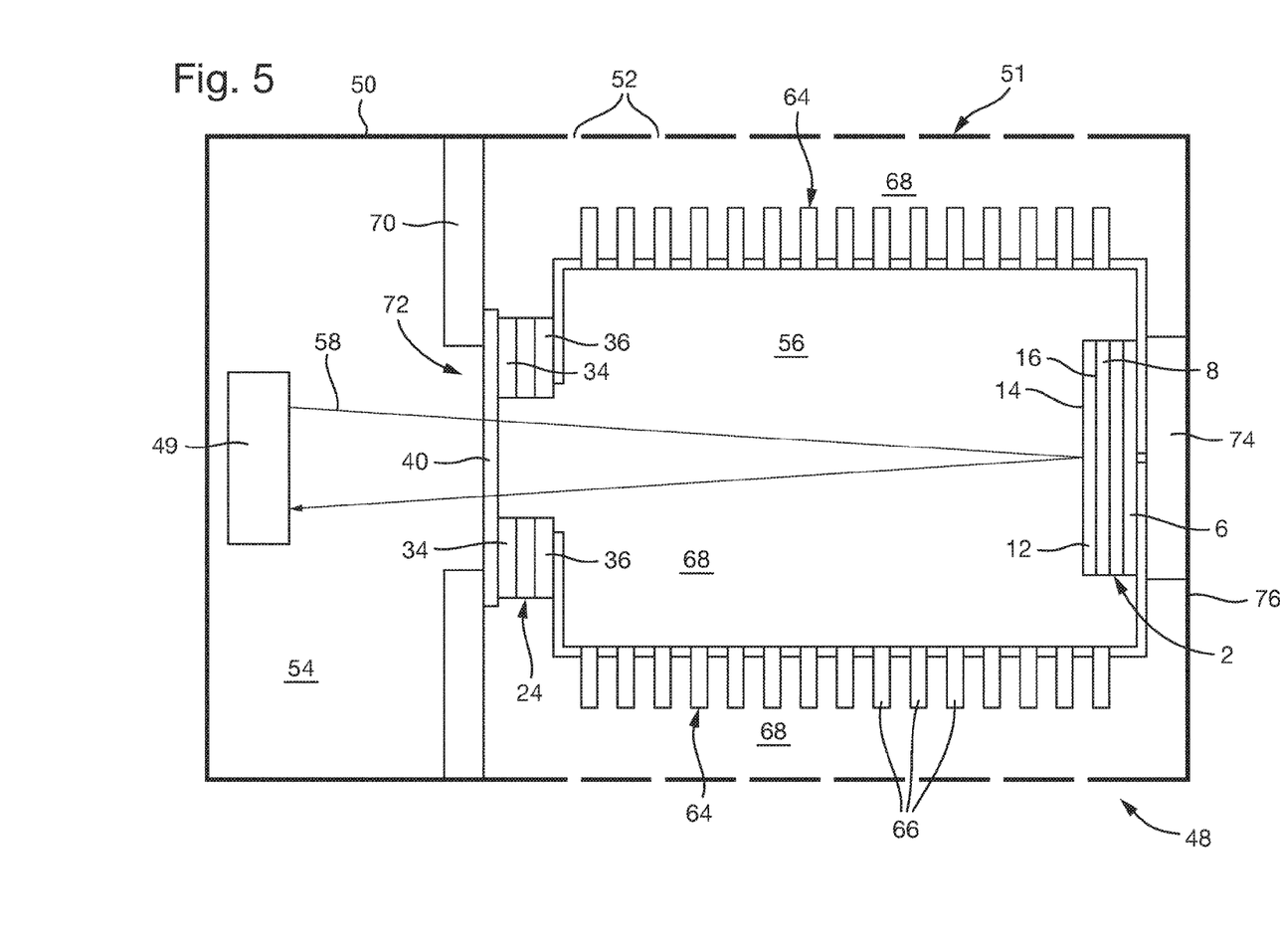
FIG. 5 shows a gas sensing apparatus in accordance with the present invention, comprising a Peltier heater according to FIG. 1 and a ring-shaped Peltier heater according to FIG. 3 for preventing condensation on a window and mirror in the gas sensing apparatus.

FIG. 5 shows a gas sensing apparatus 48 using two Peltier heaters 2, 24 in accordance with the present invention. The gas sensing apparatus 48 comprises a gas sensor 49 in a housing 50. The housing 50 includes a plastic weather cap 51, which can be removed from the housing 50, e.g. for cleaning purposes. Apart from the plastic weather cap 51, the housing 50 is made from steel. The weather cap 51 has holes 52 for the ingress of gas. The housing 50 comprises a component housing portion 54 which houses the gas sensor 49, which comprises components (e.g. control components, components for generation and detection of radiation, etc.). The components are omitted from FIG. 5 for clarity. The gas sensing apparatus 48 also comprises a measurement volume 56. During operation of the gas sensing apparatus 48, electromagnetic radiation 58 is transmitted from the component housing portion 54 into the measurement volume 56 via a window 40. The electromagnetic radiation 58 is reflected from a mirror 12 back through the window 40 to a detector (not shown).

It will be appreciated that the particular gas sensing apparatus shown in FIG. 5 is representative of a possible arrangement. The present invention can be advantageously employed in any gas sensing apparatus incorporating reflective or transmissive optical elements, or any other optical element on which condensation may form.

The window 40 is provided with a ring-shaped Peltier heater 24 as described with reference to FIG. 4 above. The Peltier heater 24 has a hot side 34 and cold side 36. The hot side 34 is attached to and in thermal contact with the window 40. The cold side 36 is in thermal contact with two heat sinks 64. The heat sinks 64 are made of metal, and have fins 66 to facilitate the absorption of heat energy from the ambient air 68 in the measurement volume 56. It will be appreciated that any number of heat sinks could be used. One heat sink could be used, e.g. extending across the top and bottom of the measurement volume 56 like the heat sinks 64 shown in FIG. 5, but being joined behind the mirror 12 and Peltier heater 2. The heat sink(s) may have holes to allow the flow of gas within the housing. Such holes may be necessary for heat sinks that substantially encapsulate part of the measurement volume 56, e.g. heat sinks having cylindrical symmetry.

When electrical power is supplied to the Peltier heater 24, heat energy is transferred from the heat sinks 64 in thermal contact with the cold side 36 to the window 40 in thermal contact with the hot side 34. In addition, Joule heating from the Peltier heater 24 generates heat that is transferred to the window 40. Accordingly, the temperature of the window 40 is raised, preventing and/or removing condensation from the window 40 as described above with reference to FIG. 4.

Due to the heat that is transferred away from the heat sinks 64, the temperature of the heat sinks drops. This has two main effects.

First, the heat sinks 64 are at a lower temperature than the ambient air 68. As a result, any water vapour in the ambient air 68 tends to condense on the relatively cool heat sinks 64. This reduces the humidity level in the ambient air, further reducing the likelihood of condensation developing on the window 40. In addition, extra heat energy is transferred to the heat sinks 64 by condensing water vapour, and that extra heat energy is transferred via the thermoelectric heat pumps 2, 24 to the mirror 12 and window 40. This additional heat energy may be help to reduce or eliminate the temperature difference between the heat sinks 64 (and therefore the cold side 36 of the Peltier heater 24) and the hot side 34 of the Peltier heater 24, significantly increasing the efficiency of the Peltier heater 24.

Second, due to the lower temperature of the heat sinks 64 compared with the ambient air 68, heat energy is transferred from the ambient air 68 to the heat sinks 64. As a consequence, the ambient air 68 is cooled, increasing the temperature difference between the window 40 and the ambient air 68. This further helps to eliminate condensation from the window 40.

The window 40 is mounted on a thermally insulating wall 70 having an aperture 72 to allow the passage of electromagnetic radiation 58 into the measurement volume 56. The thermal insulation significantly reduces the transfer of heat from the window 40 to the housing 50. The advantage of this is that the heat energy provided by the Peltier effect and Joule heating of the Peltier heater 24 is transferred to the window 40 to raise its temperature, but is prevented from being dissipated in the housing 50. It is undesirable to allow this heat energy to transfer to the housing 50, as the housing 50 (which is predominantly steel) has a high heat capacity. If the Peltier heater 24 has to heat the housing 50 as well as the window 40, a much greater amount of heat energy would need to be transferred. This would substantially reduce the efficiency of the Peltier heating arrangement. The thermal insulation of the window 40 may be achieved by other thermal insulation arrangements, e.g. the window could be mounted on a thermally insulating ring placed around a hole in a steel internal wall.

It is not essential for the window (or other optical elements) to be mounted directly on a thermally insulating mount. For example, an optical element could be mounted on a subassembly, where the subassembly may be mounted on a thermally insulating mount. This may provide an additional advantage if the subassembly incorporates components that generate heat via Joule heating (e.g. optoelectronics), as the Joule heating may contribute to the heating of the optical element.

The mirror 12 is provided with a Peltier heater 2 as described above with reference to FIGS. 1 and 2. As described above with reference to FIG. 2, the Peltier heater 2 is in thermal contact with the rear surface 16 of the mirror 12. The front surface 14 of the mirror 12 is reflective in order to reflect the electromagnetic radiation 58 back through the measurement volume 56. The hot side 8 of the Peltier heater 2 is in thermal contact with the mirror 12. The cold side 6 of the Peltier heater 2 is in thermal contact with the heat sinks 64, and is mounted on a thermally insulating block 74, which is itself mounted on a rear wall 76 of the housing 50. The Peltier heater 2 provides heat energy to the mirror via the Peltier effect and Joule heating as described above with reference to FIG. 2.

Accordingly, condensation is prevented from forming on the mirror 12 and/or is removed from the mirror 12. As described above with reference to the Peltier heater 24, the Peltier heater 2 draws heat energy from the heat sinks 64 via the cold side 6. In this way, the Peltier heater 2 helps to lower the temperature of the ambient air 68, and causes the heat sink 64 to act as a condensation trap.

For similar reasons as described above with reference to the thermally insulating wall 70, the thermally insulating mount 74 is provided to prevent the transfer of heat from the heat sinks 64 to the housing 50. As mentioned above, the housing 50 has a significant heat capacity. One advantage of the present arrangement is that heat sinks 64 draw heat from the ambient air 68 and from water vapour condensing on the heat sinks 64. This heat energy increases the temperature of the heat sinks 64, which may reduce or eliminate the temperature difference between the heat sinks 64 and the hot side 8 of the Peltier heater 2, thereby improving the efficiency of the Peltier heater 2. If the heat sinks 64 were in thermal contact with the housing 50, some of the heat energy in the heat sinks 64 may be dissipated in the housing 50. Due to the significant heat capacity of the housing 50, and the fact that the housing (like the optical elements) is likely to be colder than the ambient air in circumstances where condensation is likely, this may lower the temperature of the heat sinks 64. This may result in the heat sinks 64 becoming significantly (e.g. a few degrees) colder than the hot side 8 of the Peltier heater, reducing the efficiency of the Peltier heater 2.

Figure 6:
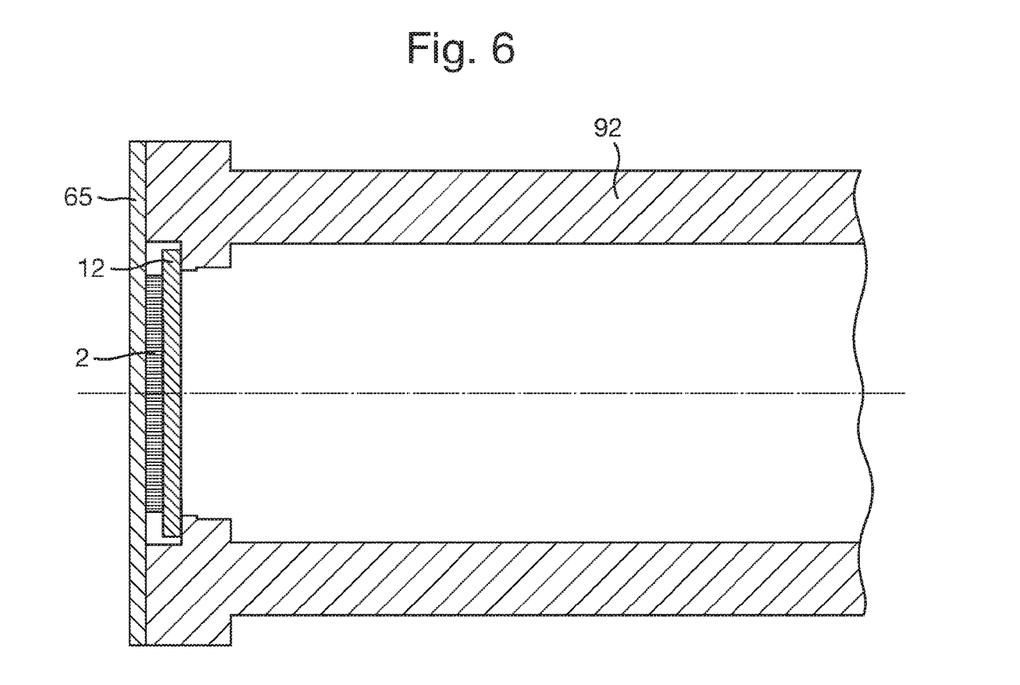
FIG. 6 shows an arrangement for holding a mirror and a Peltier heater in place with respect to a heat sink and the housing of a gas sensor in accordance with an embodiment of the invention.

FIG. 6 shows an alternative arrangement for holding the mirror 12 and Peltier heater 2 in place with respect to a heat sink 65 and the housing 50. The housing 50 is omitted in FIG. 6 for clarity. The Peltier heater 2 is in thermal contact with the mirror 12, and the Peltier heater 2 and the mirror 12 are held against the heat sink 65 by a mirror holder 92, so that the cold side of the Peltier heater 2 is in thermal contact with the heat sink 65.

As in other embodiments, the heat sink 65 may be made of any suitable material, e.g. metal or ceramic. It may have any suitable shape, e.g. a disc shape, or it may have fins. It may be porous, e.g. on the micro- or nanometer scale, e.g. it may be a microporous ceramic heat sink.

The mirror holder 92 may be made of a thermally insulating material, e.g. plastic. Alternatively, the mirror holder 92 may be made of a thermally conductive material, e.g. metal. The contact area between the mirror holder 92 and the mirror 12 may be small enough that the mirror 12 is substantially thermally insulated from the mirror holder 92.

Figure 7:
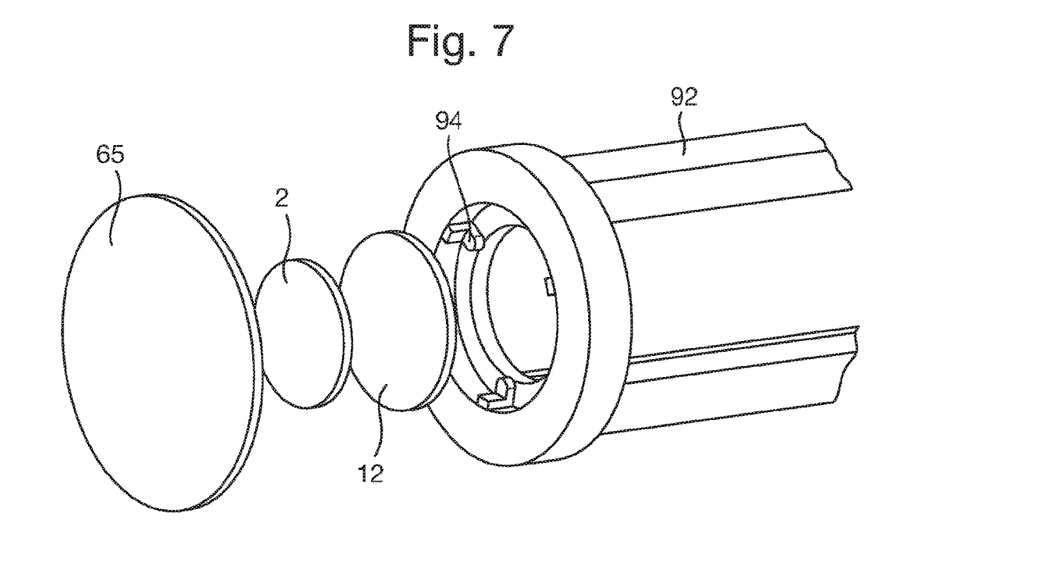
FIG. 7 shows a three-dimensional exploded view of the arrangement of FIG. 6.

FIG. 7 shows a three-dimensional exploded view of the arrangement of FIG. 6. The mirror holder 92 comprises three resting pins 94 which hold the mirror 12 and Peltier heater 2 against the heat sink 65. The resting pins substantially reduce the thermal contact between the mirror holder 92 and the mirror 12, Peltier heater 2, and heat sink 65 assembly, thereby minimizing heat transfer between the mirror 12 and the housing. More or fewer than three resting pins 94 could be used.

In some embodiments, the mirror holder 92 is made from the same material as the heat sink 65, and may be integral with the heat sink 65. In such embodiments the mirror holder may effectively act as, or part of, the heat sink. In such embodiments, the resting pins 94 serve to minimize heat transfer between the mirror and the heat sink 65 to enable the Peltier heater 2 to efficiently heat the mirror 12.

Figure 8:
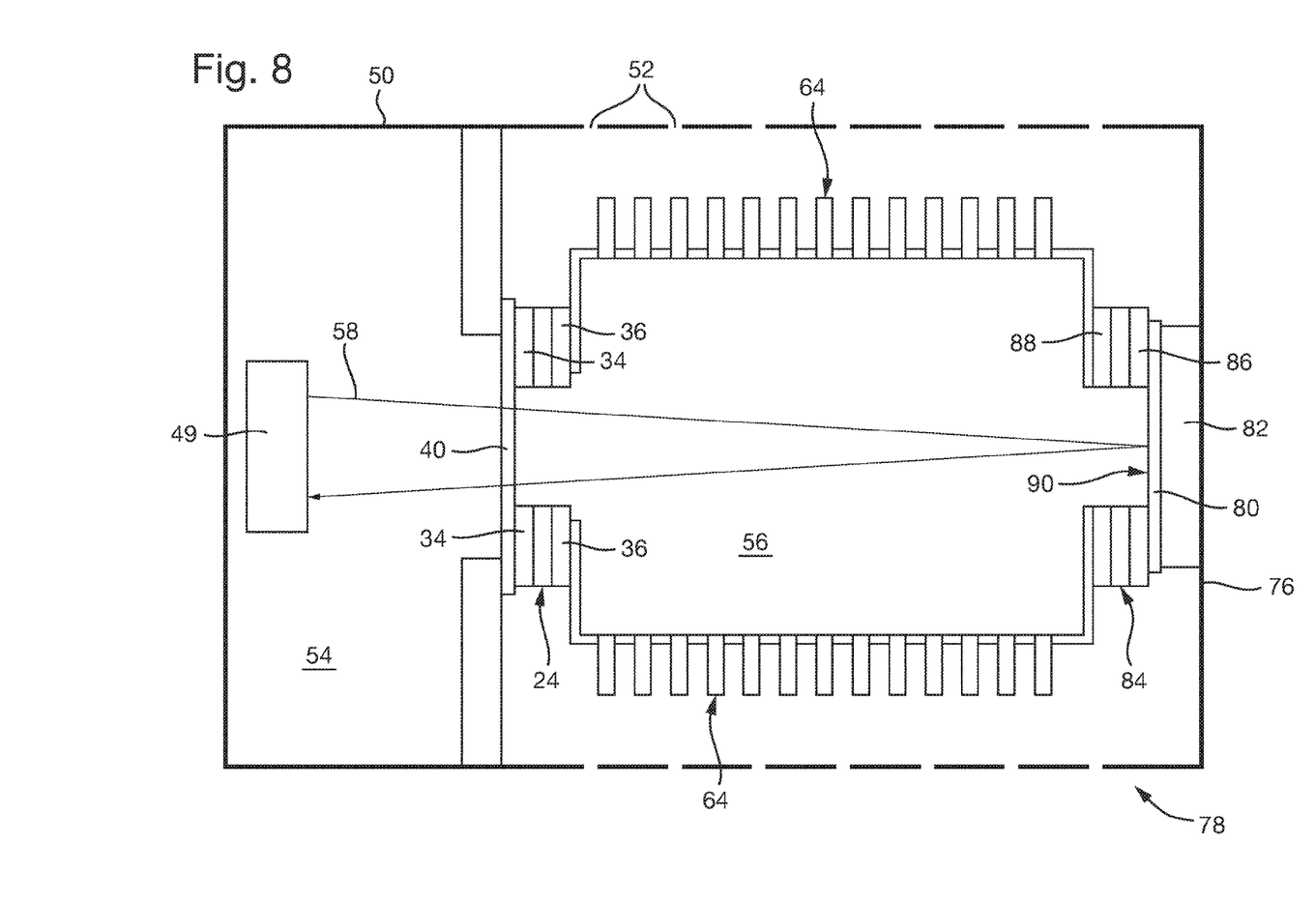
FIG. 8 shows an alternative embodiment of a gas sensing apparatus, in which two ring-shaped Peltier heaters are used for the window and mirror.

FIG. 8 shows an alternative arrangement of a gas sensing apparatus 78 with the Peltier heater 24 and window 40 in the same configuration as in the gas sensing apparatus 50, but with a different arrangement of a mirror 80 and a ring-shaped Peltier heater 84 to reflect the electromagnetic radiation back out of the measurement volume 56. The arrangement of the gas sensing apparatus 78 is otherwise identical to that of the gas sensing apparatus 50 shown in FIG. 5. The description of the elements that are identical will therefore not be reproduced.

The mirror 80 in the gas sensing apparatus 78 is positioned in a slightly different position from the mirror 12 in the gas sensing apparatus 50. The mirror 80 is mounted directly on a thermally insulating mount 82, which is mounted on a rear wall 76 of the gas sensing apparatus 78. Instead of having a Peltier heater positioned between the mirror 80 and the thermally insulating mount 82, a ring-shaped Peltier heater 84 is mounted on the front (reflecting) surface 90 of the mirror. The hole in the ring-shaped Peltier heater 84 allows electromagnetic radiation 58 to reach the reflecting surface 90 of the mirror 80, and thereby to be reflected back out of the measuring volume 56.

The Peltier heater 84 is arranged with its hot side 86 in thermal contact with the mirror 80, and its cold side 88 in thermal contact with the heat sinks 64. The ring-shaped Peltier heater 84 achieves the same effect as the Peltier heater 2 in gas sensing apparatus 50, but has a different orientation and shape to allow it to be affixed to the front surface 90 of the mirror 80.

It will be appreciated that only some possible embodiments have been described, and that other variations are possible. It will also be appreciated that due to the high efficiency of thermoelectric heat pumps, in combination with the additional Joule heating, the present invention may provide a very efficient way of preventing and/or removing condensation from optical elements in gas sensing apparatus. This advantage is particularly enhanced by the fact that only a small temperature difference is needed to remove or prevent condensation. Small temperature differences can be achieved very efficiently with thermoelectric heat pumps.

Figure 9:
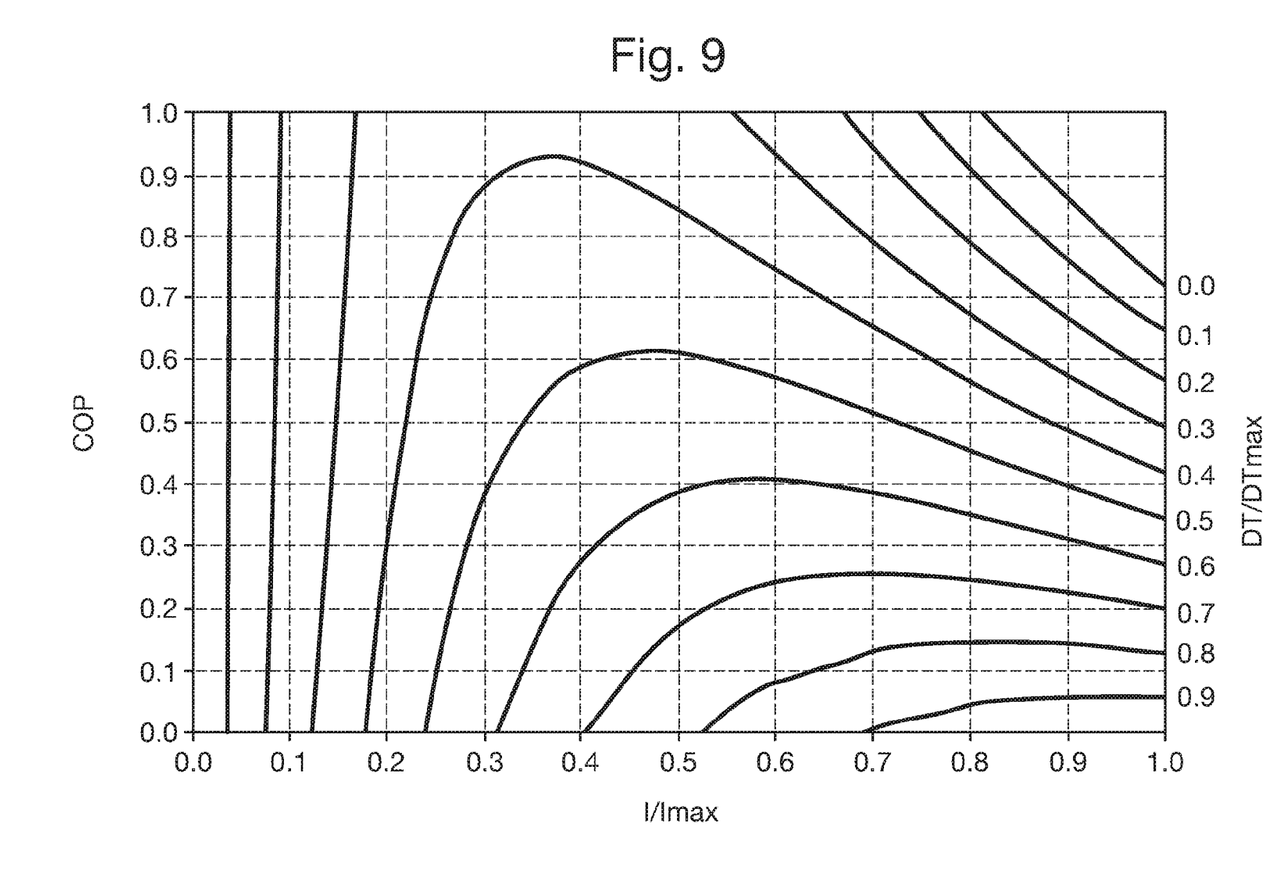
FIG. 9 shows a coefficient of performance graph for a typical Peltier heater.

This is evident from FIG. 9, which shows a coefficient of performance graph for a typical Peltier heat pump. The coefficient of performance (COP) for a Peltier heat pump is defined as follows:

$$COP = \frac{\text{heat absorbed at the cold side (Watts)}}{\text{input power of element (Watts)}}.$$

The y-axis shows the coefficient of performance, and the x-axis shows the current supplied to the Peltier heat pump. As the coefficient of performance is temperature-dependent, different graph lines are shown for different temperature differences between the hot and cold sides. The temperature differences (DT) are expressed in terms of DTmax, where DTmax is the maximum temperature difference obtainable by the Peltier heat pump. The current on the x-axis is normalised with respect to Imax, which is the current that produces a temperature difference of DTmax.

As it is only necessary to increase the temperature of the optical element by a fraction of a degree to prevent condensation, the DT/DTmax lines of interest are the upper lines (0.0-0.1). It can be seen that for a wide range of operating conditions the coefficient of performance is greater than 1.

The coefficient of performance (unlike thermal efficiency) can exceed 1 because it is the ratio of output (heat transferred by pumping) to loss (electric energy needed to drive the pumping), whereas thermal efficiency for a heat pump is the ratio of output energy to input energy.

For a resistive element that does not pump heat energy, due to energy conservation the output (heat from Joule heating) cannot exceed the loss (electric energy required to operative the resistive element). The equivalent coefficient of performance therefore cannot exceed 1 for a resistive element that does not pump heat. For a purely resistive element, the equivalent coefficient of performance is equal to 1. A Peltier heat pump therefore performs better than a resistive element for a wide range of operating conditions.

The invention claimed is:

1. A gas sensing apparatus comprising:
    a gas sensor arranged to use light to sense presence of a gas;
    an optical element arranged so that said light impinges thereon;
    a thermoelectric heat pump having a cold side and a hot side, wherein the thermoelectric heat pump is configured to transfer heat energy from said cold side to said hot side in response to a supply of electrical energy provided to the thermoelectric heat pump, and wherein the hot side of the thermoelectric heat pump is in thermal contact with the optical element;
    a measurement volume; and
    a heat sink in thermal contact with the cold side of the thermoelectric heat pump, wherein the heat sink is disposed in the measurement volume.

2. The gas sensing apparatus as claimed in claim 1, wherein the hot side of the thermoelectric heat pump is in thermal contact with the optical element(s) by virtue of being in physical contact therewith.

3. The gas sensing apparatus as claimed in claim 1, comprising a heat sink in thermal contact with the cold side of the thermoelectric heat pump, wherein the cold side of the thermoelectric heat pump is in thermal contact with the heat sink by virtue of being in physical contact therewith.

4. The gas sensing apparatus as claimed in claim 1, wherein the thermoelectric heat pump has an aperture or gap for allowing electromagnetic radiation to pass through.

5. The gas sensing apparatus as claimed in claim 1, wherein the thermoelectric heat pump is disposed in the measurement volume.

6. The gas sensing apparatus as claimed in claim 1, wherein the heat sink extends along substantially all of a length, and/or substantially all of a width, and/or substantially all of a depth of the measurement volume.

7. The gas sensing apparatus as claimed in claim 1, further comprising a housing, and wherein the optical element is thermally insulated from the housing.

8. The gas sensing apparatus as claimed in claim 1, comprising a holder holding the optical element.

9. The gas sensing apparatus as claimed in claim 8, wherein the holder is made from a thermally insulating material.

10. The gas sensing apparatus as claimed in claim 8, wherein the holder is formed as part of a heat sink in thermal contact with the cold side of the thermoelectric heat pump.

11. The gas sensing apparatus as claimed in claim 8, wherein the holder comprises a plurality of discrete retaining elements holding the optical element.

12. The gas sensing apparatus as claimed in claim 1, comprising a heat sink in thermal contact with the cold side of the thermoelectric heat pump, further comprising a housing, and wherein the heat sink is thermally insulated from the housing.

13. The gas sensing apparatus as claimed in claim 1, configured to switch on the thermoelectric heat pump intermittently.

14. The gas sensing apparatus as claimed in claim 1, configured to switch on the thermoelectric heat pump in response to an environmental condition and/or in response to the detection of a condition indicating a presence of condensation.

15. The gas sensing apparatus as claimed in claim 1, configured to switch off the thermoelectric heat pump in response to detection that condensation has been eliminated or sufficiently reduced and/or in response to a change in environmental conditions and/or once a pre-determined amount of time has elapsed.

16. A method of preventing, removing or reducing condensation on an optical element in a gas sensing apparatus, wherein the gas sensing apparatus comprises a gas sensor arranged to use light to sense presence of a gas and wherein the optical element is arranged so that said light impinges thereon, the method comprising:
    using a thermoelectric heat pump to transfer heat energy to the optical element, wherein:
        the thermoelectric heat pump has a cold side and a hot side, and the thermoelectric heat pump transfers heat energy from said cold side to said hot side in response to a supply of electrical energy provided to the thermoelectric heat pump;
        the hot side of the thermoelectric heat pump is in thermal contact with the optical element;
        the gas sensing apparatus comprises a heat sink in thermal contact with the cold side of the thermoelectric heat pump; and
        the heat sink is disposed in the measurement volume.

17. The method as claimed in claim 16, further comprising using the thermoelectric heat pump to transfer heat energy from the heat sink to the optical element.

18. The method as claimed in claim 16, wherein the thermoelectric heat pump is disposed in the measurement volume.

19. The method as claimed in claim 16, further comprising switching on the thermoelectric heat pump intermittently.

20. The method as claimed in claim 16, further comprising switching on the thermoelectric heat pump in response to an environmental condition and/or in response to a detection of a condition indicating a presence of condensation.

21. The method as claimed in claim 16, further comprising switching off the thermoelectric heat pump in response to detecting that condensation has been eliminated or sufficiently reduced and/or in response to a change in environmental conditions and/or once a pre-determined amount of time has elapsed.

* * * * *